United States Patent [19]

Lewis et al.

[11] Patent Number: 4,925,848
[45] Date of Patent: May 15, 1990

[54] DERIVATIVE OF CODEINE USEFUL AS AN AGONIST AND PROCESS FOR THE PREPARATION OF IT

[75] Inventors: John W. Lewis, North Ferriby; Colin F. C. Smith, Sproatley, both of United Kingdom

[73] Assignee: Reckitt & Colman Products Limited, London, England

[21] Appl. No.: 187,648

[22] Filed: Apr. 28, 1988

[30] Foreign Application Priority Data

May 15, 1987 [GB] United Kingdom ............... 8711558

[51] Int. Cl.$^5$ .................. A61K 31/485; C07D 489/06
[52] U.S. Cl. ........................................ 514/282; 546/40; 546/45
[58] Field of Search ................. 546/45, 40; 514/282

[56] References Cited

U.S. PATENT DOCUMENTS

4,241,066 12/1980 Kobylecki et al.
4,241,067 12/1980 Kobylecki et al. ................ 514/282

FOREIGN PATENT DOCUMENTS

1593191 7/1984 United Kingdom.

OTHER PUBLICATIONS

Smith, Life Sciences, vol. 40, No. 3, pp. 267–274 (1987).
de Stevens, ed., "Analygetics", Academic Press, New York (1965), pp. 127, 131.
Allen et al., Chemical Abstracts, vol. 74: 3754n (1971).
Allen, "Synthesis of New Codeinone and Indolinocodeinone Derivatives", Thesis submitted to Loughborough University of Technology, 09/71, cited in Index to These, vol. XXII, 1971–1972, ed., Paterson, et al., Aslib, London (1974), pp. 30–33.

*Primary Examiner*—Mukund J. Shah
*Assistant Examiner*—Diana G. Rivers
*Attorney, Agent, or Firm*—Bacon & Thomas

[57] ABSTRACT

A compound of the formula:

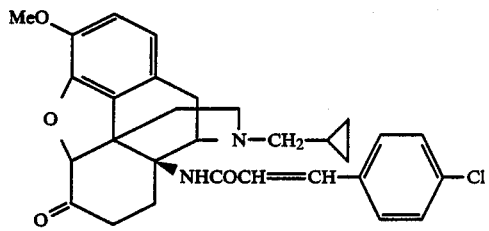

A process for its preparation and pharmaceutical compositions comprising the compound or a pharmaceutically acceptable salt thereof with a pharmaceutically acceptable diluent or carrier. The compound exhibits analgesic activity.

7 Claims, 2 Drawing Sheets

DERIVATIVE OF CODEINE USEFUL AS AN AGONIST AND PROCESS FOR THE PREPARATION OF IT

This invention relates to a derivative of codeine, to a process for its preparation and to pharmaceutical compositions thereof. According to this invention there is provided a compound of the formula:

I

In our British patent specification no. 1593191 we describe and claim 14-amino derivatives of morphine of the formula:

II in which $R^1$, $R^2$, $R^3$, $R^4$, $R^5$, $R^6$ are certain specified values and the dotted line at positions 7, 8 indicates an optional bond.

The compounds of formula II exhibited analgesic and/or antagonist activity in animal tests.

We have now investigated the structure activity relationships in a series of 14-cinnamoylamino doeinone derivatives of formula III:

III

The compound of formula I emerged from this study as a compound possessing a unique profile. A particular aspect of this study was an examination of the relative selectivity of each derivative for the different classes of opioid receptors and included some of the previously disclosed specific compounds of formula II. The vast majority of opioid drugs that are currently in clinical use as analgesic agents (e.g. morphine, fentanyl, methadone) are agonists at mu receptors. The effects of the more recent analgesic partial agonists, exemplified by buprenorphine, are also mediated through the mu receptor. It is probable that the many side effects of these drugs, e.g. nausea, respiratory depression, dependence, inhibition of gut motility and euphoria also result from their mu receptor interaction.

It is well known that compounds acting as agonists at the kappa receptor are also effective analgesic agents. In addition, however, this kappa agonism is associated with unpleasant side effects, such as dysphoria and hallucinations. The fact that endogenous opioids have been identified which possess predominantly mu (endorphins) or predominantly kappa (the dynorphins) agonist activity suggests that these endogenous substances may play a prominent role in the determination of mood (i.e. dysphoria and euphoria) via the mu and kappa receptor systems.

More recently there has been increasing evidence that delta receptor agonists mediate analgesia but there is no evidence that such a compound has any effect on mood (i.e. dysphoria or euphoria). This is in agreement with the expectation that delta agonists will possess a different side effect profile from the mu and kappa agonist. This is further supported by the finding that in contrast to mu agonists, delta agonists have no effect on gut motility (Galligan et al J. Pharm. Exp. Theraps. 229, 641, 1984).

Compounds of formula III were initially examined in two antinociceptive tests (in vivo) to assess their analgesic potential and are shown in the following Table 1. These tests were:

(1) the antiwrithing test (the H and F test) which is described in the paper Hendershot and Forsaith (J. Pharmac. Exp. Ther., 125, 237 1959) and provides a measure of sedative or analgesic activity.

(2) The rat tail pressure (RTP) which is described by Green and Young, (Br. J. Pharmac Chemother., 6,572, 1951).

Some of the compounds tested were disclosed in specification no. 1593191, and some are novel compounds; the prior compounds are indicated by their exmaple number from the earlier specification. The results obtained are set out in Table 1.

TABLE 1

| ACTIVITIES OF COMPOUNDS OF FORMULA III | | | | |
|---|---|---|---|---|
| Compound # | R | 7,8 | RTP | H and F |
| Ex. 15 | H | dehydro | 0.127 | $1.9 \times 10^{-5}$ |
|  | H | dihydro | $6 \times 10^{-4}$ | $2.75 \times 10^{-8}$ |
| Ex. 91 | Cl | dehydro | 0.88 | 7.5 |
| I | Cl | dihydro | 0.075 | $8 \times 10^{-3}$ |
| Ex. 92 | Me | dehydro | 3.35 | 0.48 |
|  | Me | dihydro | 0.08 | 0.06 |
|  | $NO_2$ | dehydro | 0.06 | 1.2 |
|  | $NO_2$ | dihydro | 0.026 | $2.8 \times 10^{-3}$ |
|  | $CF_3$ | dehydro | 3.0 | 2.48 |
|  | $CF_3$ | dihydro | 0.048 | 0.29 |
|  | Br | dehydro | 2.2 | 2.0 |
|  | Br | dihydro | 30 | $2.6 \times 10^{-5}$ |
| Ex. 90 | OMe | dehydro | >10 | >10 |
|  | OMe | dihydro | 40% at 1 mg/kg | 2.5 |
| Buprenorphine | — | — | $7.5 \times 10^{-3}$ | $7.6 \times 10^{-3}$ |
| Nalbuphine | — | — | >10 | 0.039 |

Ex = Example number from specification no. 1593191
I = Compound of formula I, the compound of this invention Surprisingly, these results show that the novel 7,8-dihydro compounds are more potent in the H and F test than the corresponding 7,8-dehydro analogues. With the exception of the p-bromo compound this was also true of the results in the RPT test, which indicate agonist activity. The above-mentioned specification no. 1593191 discloses the two compounds of formula IV:

We have foun that neither the dehydro compound (Example 49) nor the dihydro compound (Example 108) exhibited agonist activity in the RPT test.

In the rat tail flick (RTF) test situation it was reported, in a response filed during the prosecution of the U.S. application corresponding to British patent no 1,593,191, that the $AD_{50}$ values of the compounds of the said exmaples 49 and 108 (mg/kg; s.c.) were 0.132 (7,8-dehydro) and 0.16 (7-8-dihydro) indicating that there was not significant difference between the two compounds. The RTF test which was used screened for morphine antagonist activity, the method being modified from that described for mice by Ben Basssat et al (Arch. Int. Pharmacoldyn, 122,434, 1959) with he nociceptive stimulus in the test being a water bath at 55° C. This result leads to the conclusion that the degree of saturation in the 7,8 position has no effect on the potencies of the compounds.

Of particular interest are those 7,8-dihydro compounds with a potentially similar profile to the partial agonists anlbuphine and buprenorphine; i.e. a relatively high potency in the H and F test and a potency within the range of those for these two compounds in the RTP test. To obtain some insight into the profiles at opioid receptor subtypes compounds of formula III where R=H, Cl, Br and Me were therefore examined in isolated tissue preparations. Comparative data on the previously disclosed dehydro compounds of formula III is also included. The results obtained in the mouse was deferens preparation (MVD)(Henderson et al Brit J Pharmacol., 46,764, 1972) for these compounds are shown in Table 2. Although the unsubstituted compounds (R=H) were full agonists in this test situation no delta-agonist properties could be detected. No affinity values could be obtained for the compound of formula I, the compound of this invention, because in this preparation it showed delta-agonist activity. The corresponding methyl and bromo dihydro compounds were antagonists with the rank order of affinities: mu>delta>kappa.

To investigate the agonist effects of the compound of formula I in the MVD test, $IC_{40}$ values obtained in this tissue were compared with those observed in the presence of the delta selective antagonist RX 8008M which has 2 to 4 fold higher affinity for the delta-receptor than the mu receptor and negligible affinity for the kappa receptor (Smith Life Sci., 1987, 40, 267) or the mu selective antagonist naltrexone; the results are set out in Table 3.

TABLE 2

| ACTIVITIES OF COMPOUNDS OF FORMULA III | | | | | |
|---|---|---|---|---|---|
| | | | | In vitro MVD | |
| Compound | R | 7,8 | μ | k | d |
| Ex. 15 | H | dehydro | *μ and k-Agonist 200 × NM | | |
| | H | dihydro | μ Agonist 72,000 × NM | | |

TABLE 2-continued

| ACTIVITIES OF COMPOUNDS OF FORMULA III | | | | | |
|---|---|---|---|---|---|
| | | | | In vitro MVD | |
| Compound | R | 7,8 | μ | k | d |
| Ex. 91 | Cl | dehydro | No d-agonism detected Weak μ + k-Agonist $ED_{40}$ > 300 ng/ml | | |
| I | Cl | dihydro | No d-agonism detected d-Agonist $ED_{40}$ 3.1 ng/ml | | |
| Ex. 92 | Me | dehydro | Partial μ Agonist - No d agonism detected | | |
| | | | | ke (nM) | |
| | Me | dihydro | 0.28 | 66.3 | 19.3 |
| | Br | dehydro | Not determined | | |
| | | | | ke (nM) | |
| | Br | dihydro | 0.32 | 27.3 | 8.6 | ke = Molar concentration of antagonist at which twice the concentration of the agonist was required to produce the same response as that produced in the absence of the antagonist; μ Agonist = Normorphine (NM); k-Agonist = Ethylketocyclazocine; d-Agonist = D-Ala-D-Leu Enkephalin.
*In the guinea pig ileum preparation (GPI), as described on page 268 of the Smith paper referred to above, the compound is predominantly a k-agonist.

TABLE 3

| AGONIST EFFECTS OF THE COMPOUND OF FORMULA 1 IN THE MVD TEST | | |
|---|---|---|
| Dosage Group[a] | $IC_{40}$[b] ng/ml | Dose Ratio[c] |
| I | 0.098 + 0.03 | |
| I + RX 8008M (10 ng/ml) | 9.15 + 3.4 | 93 |
| I + Naltrexone (100 ng/ml) | 1.44 + 0.01 | 14.7 |

[a]Groups (n = 2–6) of MVD used in each treatment schedule.
[b]$IC_{40}$ is the concentration of agonist required to reduce the maximal contraction to electrical stimulation by 40 percent. The slow receptor kinetics of I precluded the determination of agonist $IC_{40}$ values in the presence or absence of the antagonists in the same preparation.
[c]Ratio: $IC_{40}$ of I in presence of antagonist/$IC_{40}$ of I.

The greater antagonism of the agonist effects of compound I by RX 8008M in comparison to that of naltrexone clearly demonstrates that the compound of formula I was acting predominantly on delta receptors in this tissue. None of the other compounds of Table 2 showed any detectable delta agonist efects in the MVD test indicating that compound I possesses a unique profile.

In the DMPP (dimethylphehylpiperazine) stimulated GPI preparation (kappa and mu test) the compound of formula I produced a very shallow dose-response curve which was atagonised by RX 8008M (25 nM) indicating that the compound is a low intrinsic activity mu agonist with no detectable kappa agonist activity.

In this GPI preparation the methyl dihydro compound showed predominantly kappa partial agonist activity. The bromo dihydro compound on the other hand demonstrated negligible agonist activity in both the MVD and GPI preparations.

The in vitro properties of the compound of formula I can be summarized in the following way: a substantial level of intrinsic activity at delta-receptors and low intrinsic acitivity at mu receptors. No other compound from the dihydro series or from the related dehydro series previously disclosed in specification no. 1593191 has been found to possess this profile of activity.

The results described herein are highly surprising and indicate strongly that the compound of this invention is potentially of great value in the search to provide a good strong anagesic which does not possess undesirable side effects which have so far been associated with every analgesic which has been considered as a morphine replacement. The significance of the results herein described with these tests on the compound of this invention will be appreciated when consideration is given to the enormous effort made by many research workers over many years to discover a strong analgesic with a highly desirable set of properties which can be used as a morphine replacement.

A furthe demonstration of the uniqueness of compound I is seen in self-administration studies in monkeys. Drug reinforcing effects were evaluated in rhesus monkeys trained to respond for 0.32 mg/kg/iv injection of codeine. Doses of compound of formula I were substituted for codeine in single 130 minute test sessions. The average response rates maintained by compound ( (0.0003–0.01 mg/kg, i.v.) were identical to those maintained by saline at all the doses tested as shown in the following FIG. 1. In which the lower broken line represents the saline supported response whilst the solid line is the response supported by compound I. The range of codeine responding is indicated by the area bounded by broken lines. Numbers refer to individual monkeys.

Figure 1:
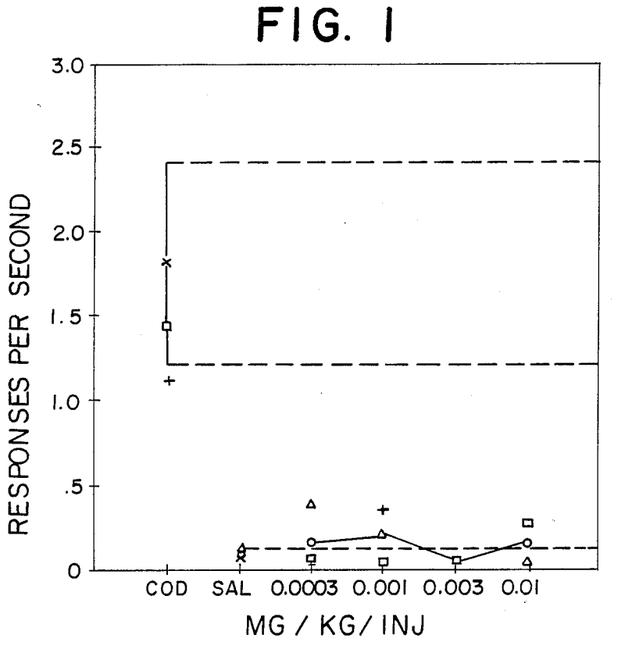

In FIG. 1,
x indicates Grand Average;
○ indicates Average;
□ indicates monkey #81;
Δ indicates monkey #1497;
+ indicates monkey #1699.

The closely related bromo and methyl dihydro compounds were also tested under similar conditions (see FIGS. 2 and 3) and in contrast to compound I both maintained response rates that were appropriately equal to the level of responding maintained by codeine. These results add support to the proposition that a compound possessing delta-agonist properties has a different side effect profile from mu and kappa agonists.

Figure 2:
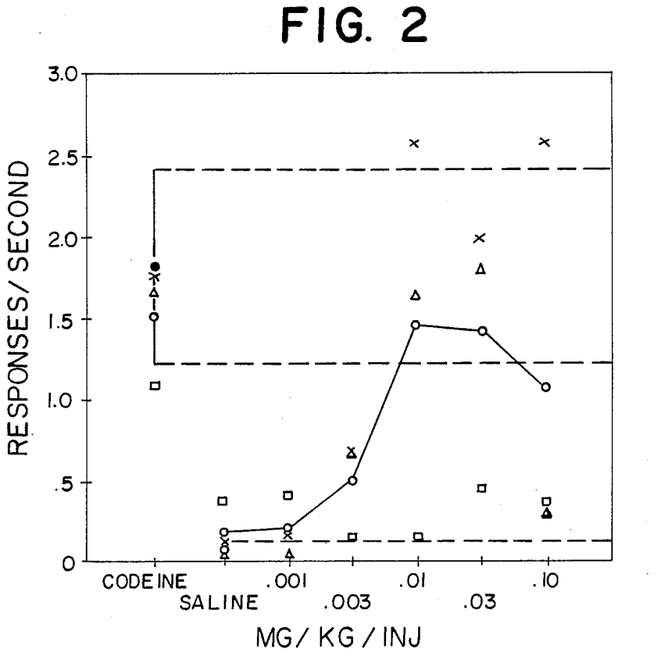

In FIG. 2,
● indicates Grand Average;
○ indicates Average;
x indicates monkey #1497;
□ indicates monkey #1719;
Δ indicates monkey #906.

Figure 3:
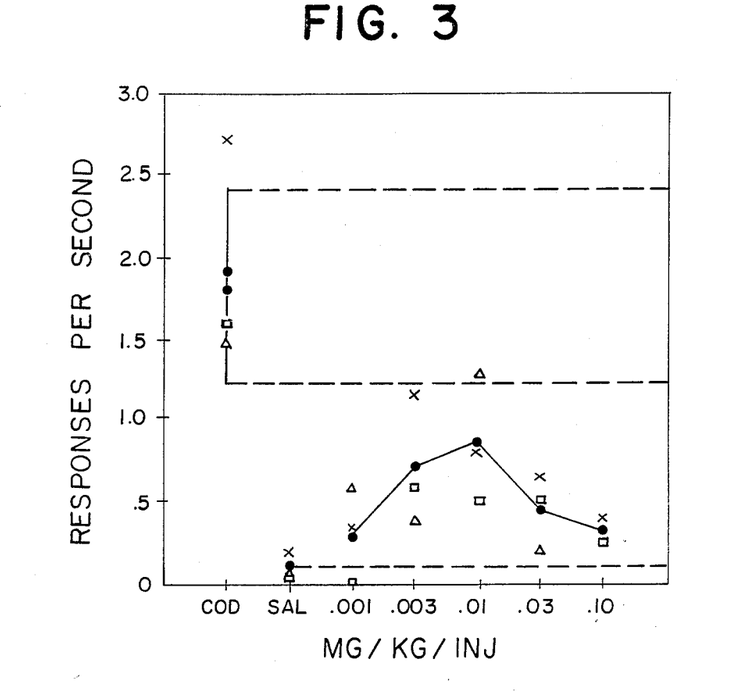

In FIG. 3,
● indicates Grand Average;
● indicates Average;
x indicates monkey #1497;
□ indicates monkey #906;
Δ indicates monkey #7730.

PREPARATION OF THE COMPOUND OF FORMULA I

The compound of formula I may be prepared by acylating the 14-β-amino compound of formula V:

V with p-chlorocinnamoyl chloride in dichloromethane. This is in contrast to the process described in our specification no. 1593191 which describes the acylation of the corresponding N-cyclopropylmethylnorthebaine derivatives. In this new process the introduction of the N-cyclopropylmethyl group is carried out in the last step of the reaction sequence. Thus N-dealkylation of compound of formula VI:

VI is achieved by using diethylazodicarboxylate in acetonitrile to give the novel compound of formula VII:

VII

This cyclic structure is conveniently hydrolysed, e.g. with 2N hytdrochloric acid in methano, to give the intermediate nor compound (as its hydrochloride salt) which, without further purification, may be alkylated with yclopropylmethyl bromide, for example in the presence of potassium bicarbonate and potassium iodide in acetone to give the compound of formula I.

Preparation of 14-β-p-Chlorocinnamoylamino7,8-dihyrocodeinone

To a stirred solution of 14-amino-β7,8-dihydrocodeinone (12 g, 0.038 mol.) in anhydrous dichloromethane (120 ml.) at 15°–25° as added p-chlorocinnamoyl chloride (7.58 g, 0.039 mol.) with water bath cooling, and the solution was allowed to stand at room temperature overnight. The solution was washed with sodium carbonate solution, dried and most of the dichloromethane was removed with vacuum. Ethanol was added and most of the solvents were removed with vacuu. The mixture was allowed to stand at room temperature for 1h and the product removed for filtration, washed with ethanol, dried at 65° C. in vacuo over phosphorus pentoxide overnight to give 14-β-p-chlorocinnamoylamino-7,8-dihydrocodeinone mp.166°–168° (17.64 g, 96% yield).

Preparation of 19-p-Chlorocinnamoyl-7,8-dihydro14-β,17-iminomethano-norcodeinone To a stirred suspension of 14-β-p-chlorocinnamoylamino-7,8-dihydrocodeinone (4.8 g, 0.01 mol.) in acetonitrile (40 ml, dry) was added diethylazodicarboxylate (2.09 g, 0.012 mol.) and the mixture was heated under reflux. Further quantities of diethylazodicarboxylate were added (350 mg, 0.002 mol.) at 1h and 2h and finally (100 mg, 0.00057 mol.) at 3h. After a further 1h heating under reflux the solution was cooled, the solvent removed with vacuum and replaced with ethanol (40 ml). The solution was kept at 0° C. overnight, the resulting precipitate was removed by filtration and dried in air to give 19-p-chlorocinnamoyl-7,8-dihydro-14-β-17-iminomethano norcodeinone. mp.240° (3.28 g, yield 69%).

Preparation of 14)-β-p-chlorocinnamoylamino-7,8-dihydronorcodeinone hydrochloride A solution of 19-p-chlorocinnamoyl-7,8-dihydro-β-14,17-iminomethanonorcodeinone (1.2 g, 0.25 mol.) in methanol (10 ml.) containing 2M hydrochloric acid (2.5 ml.) was heated under reflux for 30 min. The solvents were removed with vacuu, and residual water was removed azeotropically with toluene with vacuum. The resulting solid was dried in air to give crude 14-β-p-chlorocinnamoylamino-7,8-dihydronorcodeinone hydrochloride (1.31 g) which was used without further purification.

Preparation of 14-β-p-chlorocinnamoylamino-7,8-dihydro-N-cyclopropyl-methyl-norcodeinone (the compound of formula I)

To a stirred solution of 14-β-p-chlorocinnamoylamino-7,8-dihydronorcodeinone hydrochloride (1.1 g, 0.0022 mol.) in acetone (8 ml.) containing water (125 mg.) was added potassium iodide (540 mg, 0.00325 mol. freshly ground), potassium bicarbonate (1.21 g, 0.0121 mol.) and cyclopropylmethyl bromide (440 mg., 0.00326 mol.) and the mixture was heated under reflux for 4 hours. The mixture was cooled and the inorganic salts were removed by filtration and washed with acetone. The filtrates were combined, the solvent removed with vacuum and the residue partitioned betweendichloromethane and 5% sodium bicarbonate solution. The organic layer was dried and the solvent removed with vacuum. The residue (1.1 g) was purified on a chromatotron (Harrison Research Inc., 4 mm. SiO2 rotor) eluting with dichloromethane/methanol (gradient 0–5% methanol). The relevant fractions were collected and the solvent removed by evaporation with vacuum. The residue was titurated with a little ethanol and evaporation of the solvent followed by drying in air afforded 14-β-p-chlorocinnamoylamino-7,8-dihydro-N-cyclopropylmethyl-norcodeinone mp 127°–129° C. (650 mg, yield 57%).

The mesylate salt was found to have a melting point of 256° C. and the hydrochloride salt a melting point of 301°–302° C.

Pharmaceutical compositions according to the invention may be in a form suitable for oral, sublingual, buccal, rectal or parental administration. Such oral compositions may be in the form of capsules, tablets, granules or liquid preparations such as elixirs, syrups or suspensions. Such sublingual or buccal compositions may be in the form of tablets.

Tablets contain as active ingredient the compound of formula I (or a pharmaceutically acceptable salt thereof) in admixture with excipients which are suitable for the manufacture of tablets. These excipients may be inert diluents such as calcium phosphate, microcrystalline, cellulose, hydroxypropylmethylcellulose, lactose, sucrose or dextrose; granulating and disintegrating agents such as starch; binding agents such as strach, gelatine, polyvinylpyrrolidone or acacia; and lubricating agents such as magnesium stearate, stearic acid or talc.

Compositions in the form of capsules may contain the active ingredient mixed with an inert solid diluent such as calcium phosphate, lactose or kaolin in a hard gelatine capsule.

Compositions for rectal administration in the form of suppositories may contain in addition to the active ingredient excipients such as cocoa butter or a suppository wax.

Compositions intended for parenteral administration may be in the form of a sterile preparation, such as solutions in for example water, saline, or polyhydroxy alcohols, such as propylene glycol or polyethylene glycols.

For the purposes of convenience and accuracy of dosing the compositions are advantageously employed in unit dosage form. For oral, sublingual or buccal administration the unit dosage form may contain 0.1 to 10 mg of the compound of formula I or an equivalent amount of a pharmaceutically acceptable salt thereof. Parenteral unit dosage forms may contain from 0.1 mg to 10 mg of the said compound (or salt thereof) per 1 ml of the preparation.

It is to be understood that the invention also includes the novel compound of formula VII.

We claim:

1. A compound of the formula:

2. A process for the preparation of a compound having a formula I wherein a compound of formula VII is hydrolyzed to form the nor derivative of the compound of formula I, which is then alkylated to provide the N-cyclopropyl methyl derivative, the compound of formula I.

3. A process as claimed in claim 2, wherein the compound of formula VII is prepared by reacting the compound of formula V to form the corresponding p-chlorocinnamoyl derivatofe of formula VI thereafter compound VI isreacted with diethylazodicarboxylatte in acetonitrile to form the compound of formula VII.

4. A pharmaceutical composition in unit dosage form for delta agonist use which comprises a delta agonist effetive amount of the compound claimed n claim 1 or a pharmaceutically acceptable salt thereof, together with a pharmaceutically acceptable diluent or carrier.

5. A pharmaceutical composition as claimed in claim 4 in unit sodage form for oral, sublingual, or buccal administration comprising from 0.1 to 10 mg of the compound per unit dosage.

6. A pharmceutical composition as claimed in claim 4 in unit dosage form for parenteral administration comprising from 0.1 to 10 mg of the compuond per 1 ml of the composition.

7. A compound of the formula:

UNITED STATES PATENT AND TRADEMARK OFFICE
CERTIFICATE OF CORRECTION

PATENT NO. : 4,925,848

DATED : May 15, 1990

INVENTOR(S) : John W. Lewis, et al.

It is certified that error appears in the above-identified patent and that said Letters Patent is hereby corrected as shown below:

Column 1, beginning at line 25, change the formula from

"

"

to --

--.

Column 1, line 42, change "doeinone" to --codeinone--.

Column 1, beginning at line 45, change formula III from

"

UNITED STATES PATENT AND TRADEMARK OFFICE
CERTIFICATE OF CORRECTION

PATENT NO. : 4,925,848
DATED : May 15, 1990
INVENTOR(S) : John W. Lewis and F. C. Smith It is certified that error appears in the above-identified patent and that said Letters Patent is hereby corrected as shown below:

to --

--.

Column 3, line 13, change "foun" to --found--.

Column 3, line 15, change "RPT" to --RTP--.

Column 3, line 26, change "he" to --the--.

Column 3, line 33, change "anlbuphine" to o--nalbuphine--.

Column 3, line 41, change "was" to --vas--.

Column 4, line 44, change "(dimethylphehylpiperazine)" to -- (dimethylphenylpiperasine)--

Column 4, line 47, change "atagonised" to --antagonised--.

Column 5, line 7, change "furthe" to --further--.

Column 5, line 13, change "(" to --I--.

UNITED STATES PATENT AND TRADEMARK OFFICE
CERTIFICATE OF CORRECTION

PATENT NO. : 4,925,848

DATED : May 15, 1990

INVENTOR(S) : John W. Lewis and F. C. Smith

It is certified that error appears in the above–identified patent and that said Letters Patent is hereby corrected as shown below:

Column 6, line 30, change "hytdrochloric" to --hydrochloric--.

Column 6, line 30, change "methano," to --methanol,--.

Column 6, line 38, change "dihyrocodeinone" to --dihydrocodeinone--.

Column 6, line 42, change "as" to --was--.

Column 6, line 43, change "(7.58" to --(7.85--.

Column 10, line 6, change "n" to --in--.

Column 10, line 10, change "sodage" to --dosage--.

Signed and Sealed this

Twenty-eighth Day of April, 1992

Attest:

HARRY F. MANBECK, JR.

Attesting Officer

Commissioner of Patents and Trademarks